United States Patent [19]

Nold

[11] Patent Number: 5,051,137
[45] Date of Patent: Sep. 24, 1991

[54] PROCESS FOR DECONTAMINATION AND CLEANING OF OCULAR PROSTHESES, IN PARTICULAR CONTACT LENSES, AND APPARATUS FOR PRACTICING THIS PROCESS

[76] Inventor: Yves Nold, 9 rue du Parc, 57100 Thionville, France

[21] Appl. No.: 205,842

[22] Filed: Jun. 13, 1988

[51] Int. Cl.$^5$ ............................................. B08B 5/00
[52] U.S. Cl. .............................. 134/42; 422/186.08; 422/186.12; 422/186.14
[58] Field of Search ............... 422/186.08, 182.12, 422/186.14; 134/42

[56] References Cited

U.S. PATENT DOCUMENTS

| | | | |
|---|---|---|---|
| 580,244 | 4/1897 | Yarnold | 422/186.08 |
| 2,050,771 | 8/1936 | Wait | 422/186.08 |
| 3,150,070 | 9/1964 | Ogawa | 422/186.08 |
| 3,421,999 | 1/1969 | Corwin | 422/186.08 |
| 4,385,261 | 5/1983 | Kogelschalz et al. | 422/186.12 |
| 4,572,821 | 2/1986 | Brodard et al. | 422/186.08 |

FOREIGN PATENT DOCUMENTS

| | | | |
|---|---|---|---|
| 684064 | 12/1952 | United Kingdom | 422/186.08 |
| 803724 | 10/1958 | United Kingdom | 422/186.08 |

Primary Examiner—Asok Pal
Attorney, Agent, or Firm—Young & Thompson

[57] ABSTRACT

A process for decontamination and cleaning of ocular prostheses, particularly contact lenses and to an apparatus for practicing this process chaacterized in that it consists essentially in treating the contact lenses by dipping in an isotonic solution, disposed in a receptacle (5), by bubbling ozone produced by ionization in an ionizing tube (2) and moved by a pump (3) and a conduit (4) for connecting the ionizing tube (2) to the receptacle (5) for reception of the isotonic solution and the lenses, this bubbling being effected for a predetermined duration, preferably comprised between 30 minutes and 2 hours.

5 Claims, 2 Drawing Sheets

PROCESS FOR DECONTAMINATION AND CLEANING OF OCULAR PROSTHESES, IN PARTICULAR CONTACT LENSES, AND APPARATUS FOR PRACTICING THIS PROCESS

The present invention relates to the field of visual corrective devices, particularly the maintenance of such devices, particularly the maintenance of ocular prostheses, and has for an object a process for decontaminating and cleaning such ocular prostheses, particularly contact lenses.

The invention also has for an object an apparatus for practicing this process.

The wearing of contact lenses raises, for the user of such lenses, a problem of protection against microbial infection of the eyes, such as is necessarily associated with another problem, namely that concerning the maintenance of such lenses. Thus, such a maintenance product requires, in addition to simplicity of utilization, microbiologically effective qualities and cleaning properties.

At present there exist several processes for treating contact lenses which may be classified according to their manner of action in two categories, namely chemical and physical, which however have a number of drawbacks.

The chemical processes use isotonic and sterilizing solutions which contain preservatives such as chlorohexadine gluconate, mercury derivatives or quaternary ammonium derivatives. The use of such solutions requires, however, numerous operations dangerous to the user, and moreover these solutions are the cause of relatively numerous toxic reactions and eye irritations.

It has also been proposed to treat lenses with a 3% hydrogen peroxide solution. Such a process is effective from the point of view of destruction of germs, but requires the neutralization of the solution by a reducing agent so as to avoid causing trouble from the user's eyes.

Among these physical processes, can be cited particularly boiling, which is a process known for sterilization of water but which however presents the drawback of slowly opacifying the contact lenses due to the denaturizing of the muco-protein material.

The processes known at present therefore do not permit treating contact lenses in a simple manner and without undesirable secondary effects.

The present invention as for its object to overcome these drawbacks.

It thus has for an object, a process for decontamination and cleaning of ocular prostheses, particularly contact lenses, characterized in that it consists essentially in treating said contact lenses in an isotonic dipping solution, disposed in a receptacle, with bubbling of ozone produced by ionization in an ionizing tube and circulation by means of a pump and a connecting conduit from the ionizing tube toward the receptacle containing the isotonic solution and the lenses, this bubbling being effected for a predetermined time, preferably comprised between 30 minutes and two hours.

The invention also has for an object an apparatus for practicing this process, characterized in that it is essentially constituted by a casing enclosing an ionizing tube, of which one end is connected to an air pump, and whose other end is connected to a conduit for the produced ozone, this conduit being provided with a capillarity, by an electrical control apparatus for the ionizing tube and the air pump, and by a removable receptacle for receiving an isotonic solution and lenses to be treated, into which the capillarity of the transport conduit extends.

The invention will be better understood from the following description, which relates to a preferred embodiment, given by way of non-limiting example, and explained with reference to the accompanying schematic drawings, in which:

Figure 1:
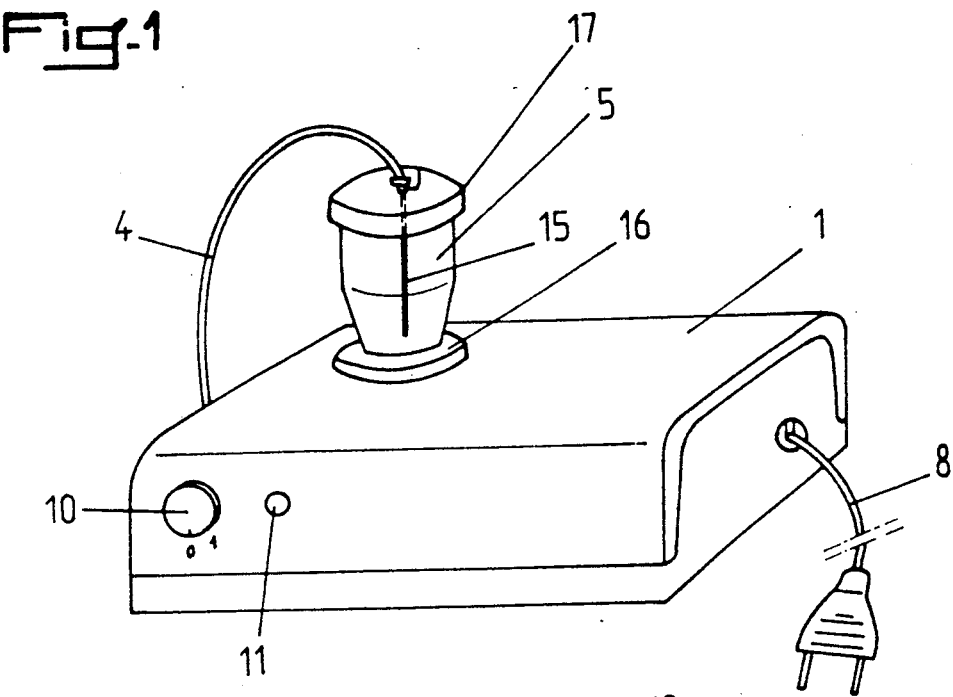
FIG. 1 is a perspective view of the device according to the invention.
Figure 2:
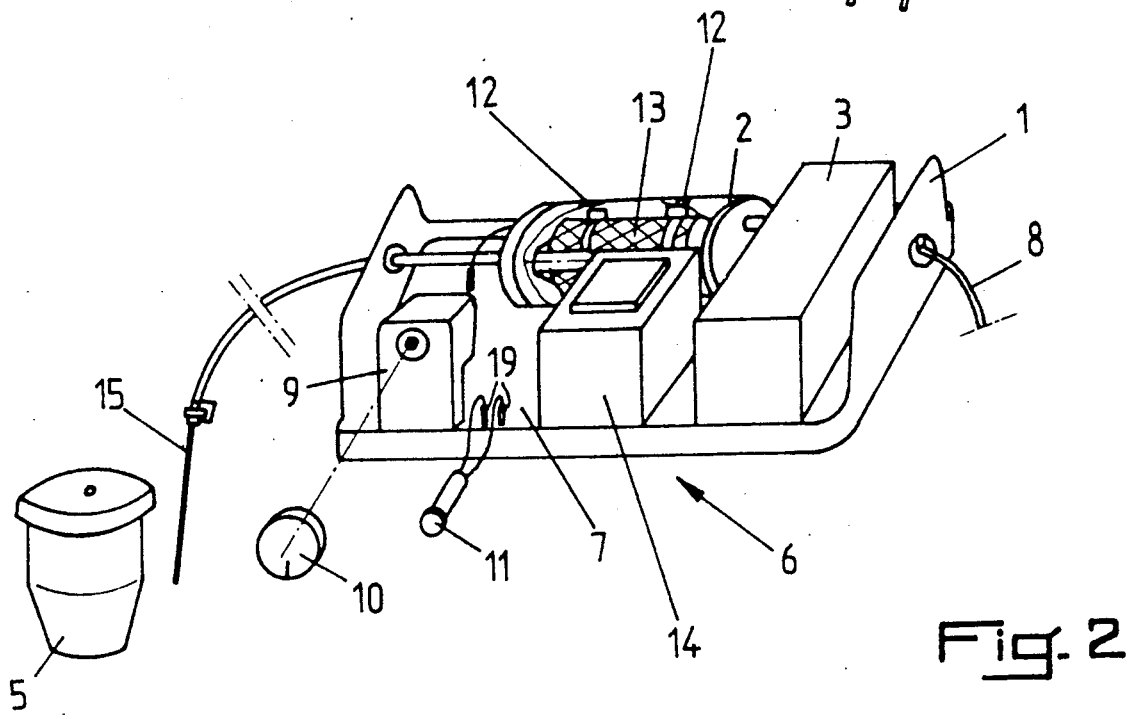
FIG. 2 is a perspective view from the front of the device of FIG. 1, the cover of the casing being removed.
Figure 3:
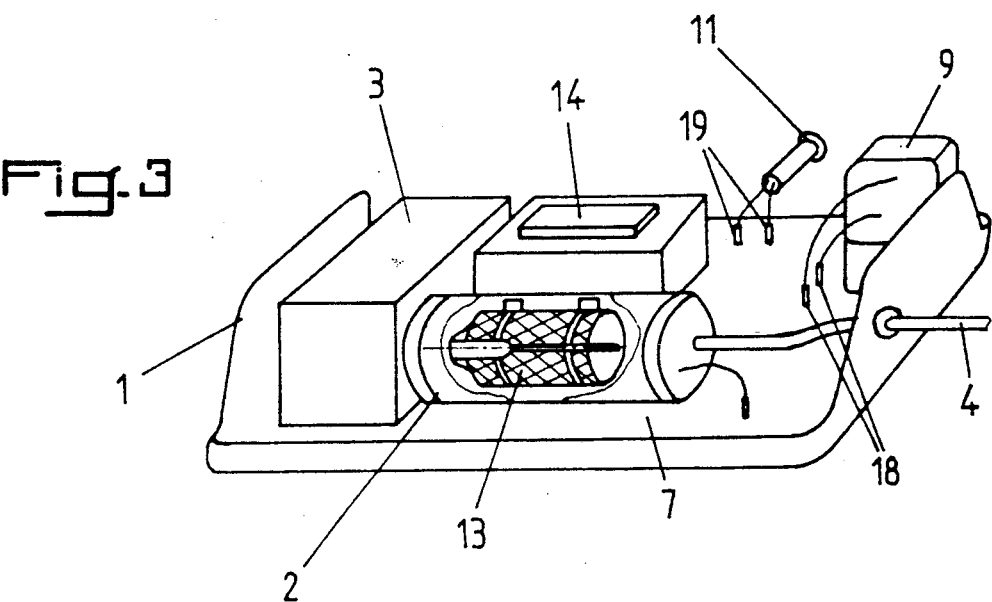
FIG. 3 is a view like that of FIG. 2, but in perspective from the rear.
Figure 4:
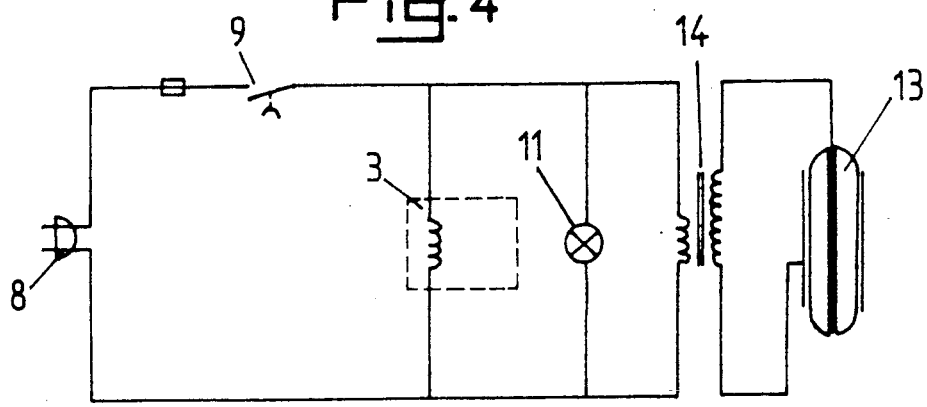
FIG. 4 is an electric control circuit diagram.

According to the invention, and as shown more particularly by way of example in FIGS. 1–3 of the accompanying drawings, the device for decontamination and cleaning of ocular prostheses, particularly contact lenses is essentially constituted by a casing 1, in which is mounted an ionizing tube 2, of which one end is connected to an air pump 3, and whose other end is connected to a conduit 4 for transporting the produced ozone, provided with a capillarity 15, and a removable receptacle 5 for receiving an isotonic solution and lenses to be treated, into which extends the capillarity 15 of the conduit 4. The ionizing tube 2 and the air pump 3 are controlled by an electrical assembly 6.

The electrical assembly 6 is constituted by a printed circuit 7 to which is connected a supply cord 8, a timer 9 which can be mechanical, electronic or the like, provided with an actuating button 10 and an indicator 11 of operation, as well as the air pump 3 and the ionizing tube 2.

The ionizing tube 2, which is fixed to the printed circuit 7 by means of clips 12, encloses an ozone lamp 13 fed by a transformer 14. Thus, when the device is placed in operation by means of button 10 and timer 9, the air pump 3 blows fresh air into the ionizing tube 2, in which said air 9 is transformed to ozone by means of the ozone lamp 13, then the air charged with ozone is pumped through conduit 4 and the capillarity 15 into receptacle 5. The removable receptacle 5 for reception of an isotonic solution and lenses to be treated is mounted on the casing 1, or against this latter, by means of a positioning disc 16, and its closure cover 17 is provided with an aperture for the introduction of the capillarity 15.

The timer 9 controlled by the button 2 is adapted to shut off electrical feed to the apparatus after a predetermined time and is connected to the printed circuit 7 by means of two connectors 18, the operation indicator 11 being also connected to the printed circuit by means of two connectors 19. The ozone utilized in the process according to the invention is a chemical agent in gaseous phase, which, under normal conditions of temperature and pressure, is constituted by three oxygen atoms and which self destructs by its tendency permanently to disassociate according to the reaction:

$$O_3 \rightarrow O_2 30\ O.$$

The oxygen atoms 0 associate two by two to form oxygen $O_2$. Thus, the ozone produced in the ionizing tube 2 disappears very rapidly when the source which generates it (ozone lamp 13) is shut off, and cannot produce a secondary effect connected to its adsorption and its ultimate discharge into the eyes of the user.

The object of the process according to the invention, is to effect the dissolution of the ozone in an isotonic solution for preservation of contact lenses, while mechanically isolating the liquid medium containing said lenses from the ionizing tube 2 which operates in a dry atmosphere.

According to a characteristic of the invention, the concentration of ozone dissolved in the isotonic solution is preferably between 0.1 mg/l and 10 mg/l, and preferably is 2.5 mg/l. Thanks to such a concentration, the device according to the invention ensures preservation from all microbiological contamination after treatment.

The operation of the device according to the invention is described hereafter, by way of example, with reference to an operation of cleaning and decontaminating lenses. After securement of the receptacle 5 on the positioning disc 16, the capillarity 15 of the conduit 4 is introduced through the cover 17 of said receptacle 5, and the electrical assembly 6 is connected to the electrical circuit by means of its feed cord 8. Then the device is set in operation by actuation of the button 10 of the timer 9 and the indicator 11 lights up. The ozone lamp 13 of the ionizing tube 2 is fed by the current from the transformer 14 and thus produces ozone which is pumped by the pump 3 through the conduit 4 and its capillarity 15, entering the receptacle 5. Because of the propulsion of the ozone by means of the pump 3, there is produced a bubbling within the receptacle 5, such that it exerts a mechanical action on the lenses, which results in loosening the deposits.

After a predetermined time of operation, for example of the order of two hours, predetermined by means of the timer 9, the cleaning and decontamination operation is terminated and the apparatus automatically shuts off.

Figure 5:
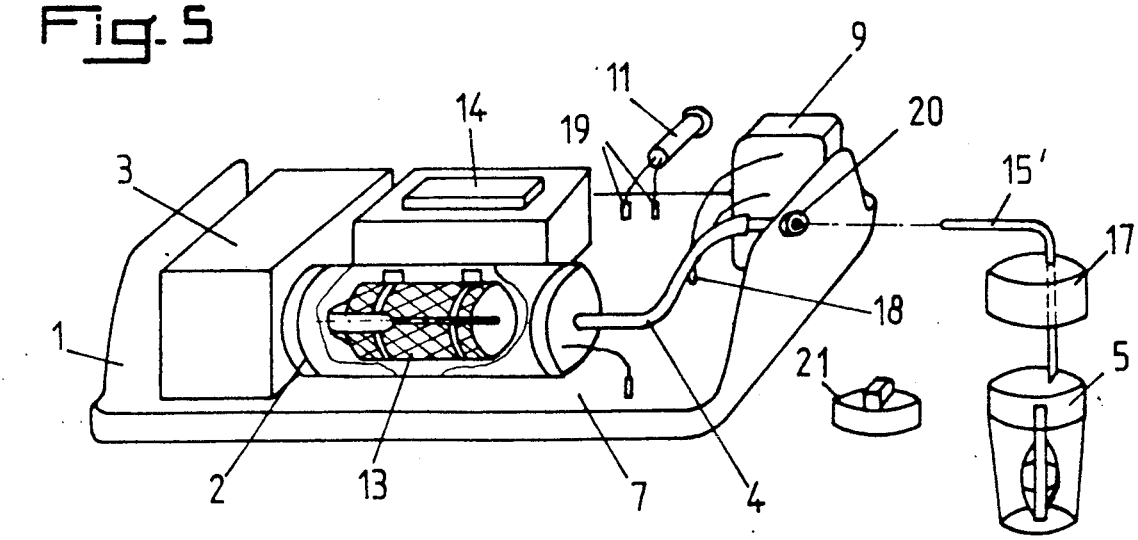
FIG. 5 is a view like that of FIG. 2 of a modified form of the invention.

FIG. 5 shows a modified embodiment of the invention, in which the conduit 4 for transport of the produced ozone, connected at one end to the ionizing tube 2, is connected at its other end to a fitting 20 opening through the wall of casing 1, and the closure cover 17 of the receptacle 5 is provided with a capillarity 15' whose external end is bent and slidably extends without play through the fitting 20 of the conduit 4. Thanks to this embodiment, it is possible to arrange the receptacle 5 directly against the casing 1 and to insert the free end of the capillarity 15' into the fitting 20 for treatment, the receptacle 5 with its cover 17 and the capillarity 15' being adapted to be separated from the casing 1 in the non-use position, such that in this position, the casing 1 has no element projecting from its walls. Moreover, the receptacle 5 may preferably be provided with a sealing plug 21 for its transportation.

Experiments have shown that the duration of treatment of two hours is sufficient for an effective cleaning and decontamination.

This experimentation was directed toward the study of bactericidal activity of microbial colonies and wild colonies of germs isolated from the conjunctiva or the lenses of persons wearing contact lenses.

The study of the bacterial activity has borne on five microbial strains, namely:
Staphylococcus aureus 209P

*Streptococcus faecalis* ATCC 10541
*Escherichia coli* ATCC 10536
*Pseudomonas aeruginosa* CNCM A22
*Candida albicans.*

To this end, the suspensions in sodium chloride solution of 9 parts per 1,000 having a titer of $10^5$ to $10^6$ germs per ml (suspension A) were prepared from cultures of 24 hours on gelose Trypcase-soya or malt agar (Candida).

EXPERIMENTAL PROTOCOL

The receptacle 5 of the apparatus is filled with 5 ml of freshly prepared microbial solution A. The bubbling of the ozone is started by means of the timer 9 which keeps the device working for two hours at the temperature of the laboratory.

At the end of the thus-programmed cycle, the suspension is diluted from 10 to 10,000 times with a sterile solution of 9 parts per 1,000 of sodium chloride. Then, 1 ml of each obtained dilution, as well as the mother solution, is incorporated in "standard gelose for census" (or in malt agar for Candida) in a Petri dish, two dishes per dilution.

At the same time, there is diluted or incorporated in the same manner a fraction of the suspension A not treated by ozone, so as to determine the initial concentration of living microorganisms (control), and the dishes are maintained at 37° C. or 30° (Candida) for at least 48 hours before proceeding with the census of the colonies.

The results shown in the following table show excellent bacterial activity with respect to the four bacterial strains and the yeast strain tested. Thus, the number of survivors has been reduced by at least four powers of 10 and even more than five powers of 10, in most cases with the bacteria, at the end of two hours of treatment by ozone by means of the apparatus according to the invention.

| Strain | Test No. | No. of Bacteria (or yeast)/ml Initial | Survivors |
| --- | --- | --- | --- |
| S. aureus 209 P | 1 | $0.25 \times 10^6$ | 0 |
| E. Coli | 2 | $1.26 \times 10^6$ | 0 |
| ATTCC 10536 | 3 | $1.00 \times 10^6$ | 0 |
| S. Faecalis | 4 | $2.16 \times 10^6$ | 0 |
| ATTCC 10541 | 5 | $0.53 \times 10^6$ | 0 |
| P. aeruginosa | 6 | $0.55 \times 10^6$ | 0 |
| CNCM A 22 | 7 | $0.55 \times 10^5$ | 0 |
| C. albicans | 8 | $0.82 \times 10^5$ | 0* |
|  | 9 | $0.60 \times 10^5$ | 0* |

*3 survivors

The apparatus according to the invention has shown excellent microbicidal efficiency, not only on the four bacterial strains examined but also on the strain of yeast Candida albicans, under normal operating conditions.

Moreover, the lenses were subjected to wild strains of selected isolated germs known to provoke serious ocular infections or to attack the lenses (Cephalosporium), namely, six bacteria:
Staphylococcus aureus
Acinetobacter calcoaceticus sp. anitratus
Pseudomonas aeruginoas
Klebsiella pneumoniae
Enterobacterr agglomerans
Serratia marcescens,
and on two molds:
Candida albicans

*Cephalosporium sp.*

For the bacteria, the culture was produced in 24 to 48 hours at 37° C. in a 10% $CO_2$ atmosphere, on an enriched chocolate gelose medium (Pasteur), and for the molds at 26° C. in a Sabouraud medium on a Petri dish, a first reading being effected at the beginning of three days, and a second reading at the beginning of seven days, for Cephalosporium.

The suspension of bacteria or yeast or spores at a concentration of about $10^5$ ml was effectuated in sterile physiologic serum, and hydrophilic lenses (70%) were immersed in this solution, then placed on their support. This latter is then introduced into a receptacle 5 filled with physiologic serum containing the suspension.

An inoculation of 50 $\mu$l of the undiluted suspension of germs and inoculations of dilutions of $10 \times 10$ of this suspension are provided in the corresponding culture medium and serve as reference for the final census of the germs which take par in the tests.

The device according to the invention is thus placed in operation, and at the end of its cleaning cycle there is seeded 50 $\mu$l of physiologic serum containing the suspension of germs and a seeding of the lenses by passage at the surface of the culture medium. The seeding media are cultivated under the conditions described above.

The following table indicates the result of the cultures, after the disinfection cycle:

| Germs | Suspension | Right Lens | Left Lens |
| --- | --- | --- | --- |
| *Staphylococcus a.* | Sterile | Sterile | Sterile |
| *Acinetobacter c.* | Sterile | Sterile | Sterile |
| *Pseudomonas a.* | Sterile | Sterile | Sterile |
| *Klebsiella p.* | Sterile | Sterile | Sterile |
| *Enterobacter a.* | Sterile | Sterile | Sterile |
| *Serratia m.* | Sterile | Sterile | Sterile |
| *Candida a.* | Sterile | Sterile | Sterile |
| *Cephalosporium sp.* | Sterile | Sterile | Sterile |

As this table shows, the decontamination of the liquid and of the lenses relative to the germs tested is complete after the cleaning cycle of the device, no surviving germ having been detected.

Moreover, supplemental tests of 100 hours continuous treatment on various types of lenses did not produce any modification of the infrared spectrum due to alteration of the material.

The process and the device according to the invention thus permit effecting the cleaning and decontamination of contact lenses in an effective manner and without undesirable secondary effects. Moreover, .5 minutes after shutting off the device, the ozone has disappeared from the aqueous solution.

The ozone production, as a function of time of operation of the device, has been determined by 0.01N sodium thiosulfate and is as follows:

0 to 20 minutes . . . 552 $\mu$g ozone/5 ml
0 to 40 minutes . . . 872 $\mu$g ozone/5 ml
0 to 60 minutes . . . 1,450 $\mu$g ozone/5 ml
0 to 120 minutes (i.e. one complete cycle) 2,460 $\mu$g ozone/5 ml Thanks to the invention, it is possible to effect effective decontamination and cleaning of ocular prostheses, particularly contact lenses, by means of a device of small size and low cost.

Of course, the invention is not limited to the embodiment disclosed and shown in the accompanying drawings. Modifications remain possible, particularly as to the construction of the various elements, or by substitution of technical equivalents, without thus departing from the field of protection of the invention.

I claim:

1. Apparatus for decontamination and cleaning of ocular prostheses, comprising a casing enclosing an ionizing tube whose one end is connected to an air pump and whose other end is connected to a conduit for transporting the ozone product, this conduit terminating in a capillary tube, an electrical assembly for controlling the ozonizing tube and the air pump, and a removable receptable having a removable lid, said receptacle having an open top adapted to be closed by said lid, said capillary tube being insertable through and withdrawable from an opening through said lid to and from a position in which a free end of said capillary tube is disposed adjacent the bottom of the receptacle.

2. Apparatus as claimed in claim 1, the electrical circuit comprising a printed circuit to which is connected a feed cord, a timer having an actuating button and an indicator indicating operation both of the air pump and of the ionizing tube.

3. Apparatus as claimed in claim 2, the ionizing tube being secured to the printed circuit by means of clips and enclosing an ozone lamp fed by a transformer.

4. Apparatus according to claim 1, in which the removable receptacle is mounted on the casing by means of a positioning disk.

5. Apparatus for decontamination and cleaning of ocular prostheses, comprising a casing enclosing an ionizing tube whose one end is connected to an air pump and whose other end is connected to a conduit for transporting the ozone product connected to an end of the ionizing tube and connected at its other end to a fitting opening through the wall of the casing, an electrical assembly for controlling the ozonizing tube and the air pump, and a removable receptacle having a removable lid, said receptacle having an open top adapted to be closed by said lid, and a capillary tube extending through said lid to adjacent the bottom of the receptacle, said capillary tube having an end above said lid which is bent and slidably penetrates without play through said fitting of the conduit.

* * * * *